April 25, 1961 F. C. REIMER Plant Pat. 2,054

PEAR TREE

Filed July 5, 1960

WITNESS

Addison J. Avery

INVENTOR

Frank C. Reimer

Webster & Webster

ATTYS.

United States Patent Office

Plant Pat. 2,054
Patented Apr. 25, 1961

2,054

PEAR TREE

Frank C. Reimer, 436 N. Holly St., Medford, Oreg.

Filed July 5, 1960, Ser. No. 40,980

1 Claim. (Cl. 47—62)

This invention relates to a new and distinct variety of pear tree which bears large, white-fleshed fruit having smooth, glossy skin which is a yellow ground color substantially overspread with red; the fruit being of the best market quality by reason of its characteristics, as will hereinafter appear.

The variety was originated by me—under close control, and in the course of certain plant breeding activities—in an orchard located near Medford, Oregon. The variety is a cross between the Comice (unpatented, and the pistillate parent) and the Max Red Bartlett (United States Plant Patent No. 741).

Seed from such cross was planted by me, in the yard of my residence in Medford, Oregon, and the present variety is a resultant seedling of such planting. When such seedling bore fruit I recognized its excellent and distinctive qualities, and selected the variety for asexual reproduction.

Such asexual reproduction of the variety was accomplished by me by top-grafting on a mature tree in the above mentioned orchard, and such reproduction—in comparison to the parent seedling—ran true in all respects, as have subsequent reproductions by top-grafting.

In comparison with the Max Red Bartlett, which is one of its parents, and which it resembles in general but superficially, the present variety is distinctively characterized by a considerably later harvest. When picked at the same stage of ripening the Max Red Bartlett has a harvest from August 10th to 20th, whereas the present variety is in harvest from September 5th to 15th. Additionally, the fruit of the present variety of pear tree is sweeter and of better quality; the fruit being entirely free from stone (grit) cells, while the Max Red Bartlett contains many. Further, the fruit of the present variety has a much longer shelf life than the Max Red Bartlett, and keeps in cold storage fully a month longer.

Figure 1:
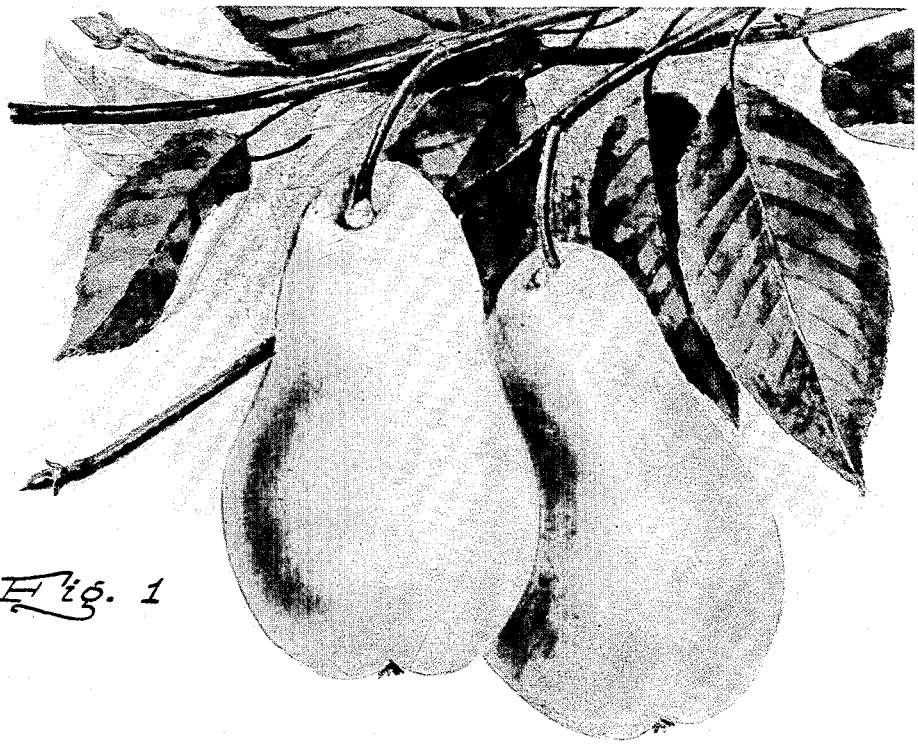
Fig. 1 is an elevation showing two of the fruit, together with twigs and leaves.
Figure 2:
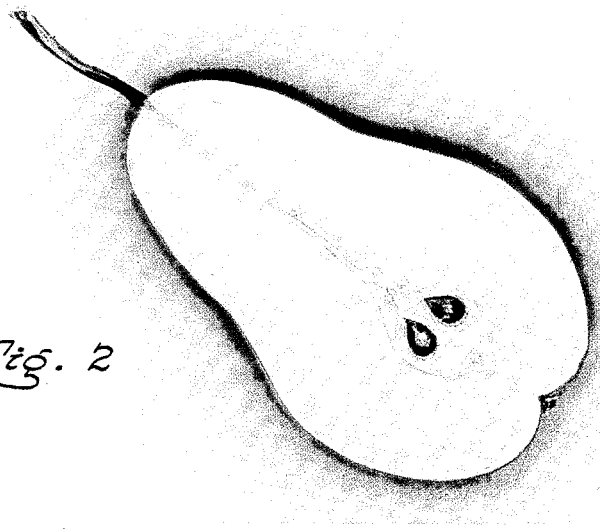
Fig. 2 is a sectional elevation of one of the fruit, with the seeds remaining in place.

Referring to pomological details of this new and distinct variety of pear tree and its fruit, the following is an outline description thereof; all major color plate identification being by reference to Maerz and Paul Dictionary of Color, except where common terms of color definition are employed.

Tree:

*Size.*—Medium to large.
*Vigor.*—Moderate to vigorous.
*Form.*—Upright; tall; vase formed.
*Growth.*—Moderate.
*Hardiness.*—Hardy.
*Production.*—Productive.
*Bearing.*—Regular bearer.

Trunk:

*Form.*—Straight.
*Size.*—Medium
*Texture.*—Medium.

Branches:

*Main branches.*—Upright, spreading; straight, thick; strong.
*Lateral branches.*—Spreading, horizontal; slender to medium thick; smooth. Color—carbuncle (8–L–7).
*Lenticels.*—Numerous; conspicuous; small; oblong to spindle form. Color—cinnamon brown.

Leaves:

*Size.*—Medium. Average length—2¾″ to 3″. Average width—1¾″ to 2″.
*Form.*—Ovate to oblong-ovate.
*Apex.*—Varying from taper pointed to abruptly pointed.
*Thickness.*—Medium, with midrib slightly depressed on the upper side and exerted and conspicuous on the lower side.
*Pubescence.*—None.
*Texture.*—Smooth.
*Margin.*—Crenate-serrate (teeth small).
*Petiole.*—Slender. Medium length and thickness, averaging 1½″ in length.
*Color.*—Top side—medium green (22–L–6). Under side—lighter green (21–K–3).

Flowers:

*Blooming period.*—April 5th to 20th. Average as compared to other commercial varieties.
*Size.*—Large; average 1½″ in diameter.
*Color.*—White.
*Petals.*—Obovate; broad; tips slightly incurved. Color.—white, with slightly pink tips upon first opening.
*Fertility.*—Fertile, but requires cross-pollination for crop excellency.

Fruit:

*Date of first picking.*—September 5th.
*Date of last picking.*—September 15th.
*Retention.*—Hangs well.
*Size.*—Large. Average length—3⅜″. Average width—2½″. Uniform.
*Form.*—Long; pyriform; symmetrical; uniform.
*Stem.*—Medium length; medium thickness. Average length—1⅜″ to 1½″. Straight to slightly curved. Base often slightly fleshy and slightly lipped. Color—carbuncle (8–L–7).
*Cavity.*—Very small; shallow; narrow; symmetrical.
*Calyx.*—Small; upright; closed.
*Lobes.*—Closed; medium length; medium breadth; acute; base slightly fleshy. Color—reddish.
*Basin.*—Small; shallow, medium width; symmetrical; very slightly ribbed.

Skin:

*Texture.*—Smooth; glossy.
*Color.*—Yellow ground color (9–L–3 to 9–L–7), substantially overspread with red (2–K–10 to 3–L–2 shading in the darkest area to 5–L–6). Cavity and surrounding basal end usually cinnamon russet.

Flesh:

*Color.*—White (10–A–1 to 10–B–1).
*Texture.*—Very fine grained; tender; very juicy; entirely free from stone (grit) cells.
*Flavor.*—Mildly subacid to sweet; sprightly.
*Eating quality.*—Best; very delicious.

*Core.*—Extremely small; closed; slender; elliptical; bluntly pointed at upper end and long pointed at lower end; fleshy between seeds.

*Calyx tube.*—Length—narrow. Width—narrow.

*Seed.*—Medium size; plump; obovate; very short point. Color—bracken (8–C–12).

Use: Market; dessert; shipping.

Keeping quality: Good. Longer shelf life than Max Red Bartlett, and keeps in cold storage fully a month longer.

Shipping quality: Good.

The pear tree as herein described may vary in slight detail due to climatic and soil conditions under which the variety may be grown; the present description being premised on reproductions grown in southern Oregon.

The following is claimed:

A new and distinct variety of pear tree, as illustrated and described, which bears white-fleshed fruit having a yellow ground color substantially overspread with red, characterized—in comparison to the Max Red Bartlett—by a materially later harvest and which on the average exceeds three weeks; by very fine grained flesh which is sweeter, more juicy, and entirely free of stone cells; and by a longer shelf life, keeping in cold storage fully a month longer.

No references cited.